United States Patent
Chiquet-Ehrismann et al.

(10) Patent No.: US 8,642,280 B2
(45) Date of Patent: Feb. 4, 2014

(54) TENEURIN AND CANCER

(75) Inventors: Ruth Chiquet-Ehrismann, Prattein (CH); Daniela Kenzelmann Brož, Küssnacht (CH)

(73) Assignee: Novartis Forschungsstiftung Zweigniederlassung Friedrich Miescher Institute for Biomedical Research, Basel (CH)

( * ) Notice: Subject to any disclaimer, the term of this patent is extended or adjusted under 35 U.S.C. 154(b) by 181 days.

(21) Appl. No.: 13/126,802

(22) PCT Filed: Nov. 6, 2009

(86) PCT No.: PCT/EP2009/064723
§ 371 (c)(1),
(2), (4) Date: Jun. 13, 2011

(87) PCT Pub. No.: WO2010/052288
PCT Pub. Date: May 14, 2010

(65) Prior Publication Data
US 2011/0229494 A1    Sep. 22, 2011

(30) Foreign Application Priority Data
Nov. 7, 2008   (EP) ..................................... 08168610

(51) Int. Cl.
*G01N 33/574*   (2006.01)
(52) U.S. Cl.
USPC ....................................................... 435/7.23
(58) Field of Classification Search
None
See application file for complete search history.

(56) References Cited

FOREIGN PATENT DOCUMENTS

| WO | WO 02/057453 A | 7/2002 |
| WO | WO 2004/036213 A | 4/2004 |
| WO | WO 2006/055704 A | 5/2006 |
| WO | 2006/104978 | * 10/2006 |
| WO | WO 2006/104978 A | 10/2006 |

OTHER PUBLICATIONS

Tucker et al, "Teneurins: A conserved family of transmembrane proteins involved in intercellular signaling during development", Developmental Biology, vol. 290, No. 2, pp. 237-245 (Feb. 15, 2006).
Feng K et al, "All four members of the Ten-m/Odz family of transmembrane proteins form dimers", Journal of Biological Chemistry, vol. 277, No. 29, pp. 26128-26135 (Jul. 19, 2002).
Rubin BP et al, "Teneurin 2 is expressed by the neurons of the thalamofugal visual system in situ and promotes homophilic cell-cell adhesion in vitro", Development, vol. 129, No. 20, pp. 4697-4705 (Oct. 1, 2002).
Kenzelmann, D., et al., "Teneurin-1 is Expressed in Interconnected Regions of the Developing Brain and is Processed In Vivo", BMC Developmental Biology, vol. 8, No. 30, Mar. 25, 2008.
Kenzelmann Broz, D. et al., "The Expression of Teneurin-4 in the Avian Embryo: Potential Roles in Patterning of the Limb and Nervous System", Int. J. Dev. Biol., vol. 54, pp. 1509-1516, (2010).

* cited by examiner

*Primary Examiner* — Sheela J Huff
(74) *Attorney, Agent, or Firm* — Hoxie & Associates LLC

(57) ABSTRACT

The present invention relates to a method for treating cancer, for instance brain tumors, in a subject by inhibiting a teneurin by administering to said subject a therapeutically effective amount of a modulator of said teneurin, for example a specific antibody or a siRNA. The present invention also encompasses methods of diagnosing cancer by measuring levels of teneurin.

3 Claims, 4 Drawing Sheets

SEQUENCE LISTING

<160> NUMBER OF SEQ ID NOS: 3

<210> SEQ ID NO 1
<211> LENGTH: 36
<212> TYPE: DNA
<213> ORGANISM: homo sapiens

```
<400> SEQUENCE: 1
cggcagactg ggctcaatga gtcggtggat aactgc                              36

<210> SEQ ID NO 2
<211> LENGTH: 36
<212> TYPE: DNA
<213> ORGANISM: Homo sapiens

<400> SEQUENCE: 2
gcagttatcc accgactcat tgagcccagt ctcccg                              36

<210> SEQ ID NO 3
<211> LENGTH: 54
<212> TYPE: DNA
<213> ORGANISM: Homo sapiens

<400> SEQUENCE: 3
tagtgcggcc gcttagtgat ggtgatggtg atgatcattg tctttgctgt cacc          54
```

TENEURIN AND CANCER

FIELD OF THE INVENTION

The present invention relates to a method of treating cancer.

This application is a National Stage Application of PCT/EP2009/064723, filed Nov. 6, 2009, which claims benefit of EP application 08168610.7, filed Nov. 7, 2008.

BACKGROUND OF THE INVENTION

Teneurins are a family of type II transmembrane proteins originally discovered in *Drosophila*. The first member was Ten-a (Baumgartner and Chiquet-Ehrismann (1993) Mech Dev 40: 165-76; Minet and Chiquet-Ehrismann (2000) Gene 257: 87-97), which was found in a search for *Drosophila* homologues of tenascins and shares with this protein family the same type of EGF-like repeats. The second member of the teneurin family, *Drosophila* Ten-m/Odd oz (Odz; Baumgartner et al. (1994) Embo J 13: 3728-40) is expressed in seven stripes during the blastoderm stage of early embryos. Mutational analysis showed that ten-m/odz is a member of the "pair-rule" gene family and encodes for an extracellular protein having a central role in determining the segmentation of the embryo. The expression pattern in the developing embryos and the adult fly suggest further important activities of this protein in later developmental processes since its presence often coincides with locations of morphogenetic cell movements, in particular, during gastrulation, the development of the tracheal system, on pioneering axons and in the developing eye (Baumgartner et al. (1994) Embo J 13: 3728-40); (Levine et al. (1994) Cell 77: 587-98); (Levine et al. (1997) Dev Dyn 209: 1-14).

Vertebrates contain four ten-a/ten-m homologues, termed ten-m1-4 (Oohashi et al. (1999) J Cell Biol 145: 563-77), odz1-4 (Ben-Zur et al. (2000) Dev Biol 217: 107-20), or teneurin 1-4 (Minet and Chiquet-Ehrismann (2000) Gene 257: 87-97), respectively. A recent study presented two new members of this family of proteins in chicken, namely, teneurin-1 and teneurin-2. Both the *Drosophila* and chicken proteins are expressed in early stages of embryonic development, in particular, in the developing nervous system and suggest an interaction or teneurin-2 with the cytoskeleton. Expression of recombinant teneurin-2 in a neuroblastoma cell line appears to lead to filopodia formation and enlarged growth cones (Rubin et al. (1999) Dev Biol 216: 195-209).

Mouse DOC4, the first vertebrate member of the teneurin family, was identified in a screen for proteins that were expressed in response to perturbation of protein folding in the endoplasmic reticulum (Wang et al. (1998) Embo J 17, 3619-30). Mouse DOC4 and all other vertebrate teneurins identified—namely, the mouse teneurins ten-m1-4/odz1-4 (Oohashi et al. (1999) J Cell Biol 145: 563-7); (Ben-Zur et al. (2000) Dev Biol 217: 107-20), the rat teneurin-2 orthologue, neurestin (Otaki and Firestein (1999) Dev Biol 212: 165-81), the chicken teneurins-1, -2 and -4 (Minet et al. (1999) J Cell Sci 112: 2019-32); (Rubin et al. (1999) Dev Biol 216: 195-209); (Tucker et al. (2000) Mech Dev 98, 187-91); (Tucker et al. (2001) Dev Dyn 220: 27-39) and the zebrafish Ten-m3 and Ten-m4 (Mieda et al. (1999) Mech Dev 87, 223-7)—were found to be prominently expressed in specific regions of the central nervous system.

Except for transcript localization by in situ hybridization in the nervous system and the possible involvement of teneurin-2 in the organization of the actin cytoskeleton in neuroblastoma cells, very little is known about the distribution and function of teneurins. Teneurins are known to be transmembrane proteins and are postulated to be involved in signal transduction. It has been suggested that teneurins could function as receptor proteins transmitting signals to the cell interior upon homo- or heterophilic binding of a ligand or as a membrane-bound ligand. Teneurin-2 is thought to be cleaved at the cell membrane either releasing a large part of the extracellular domain from the cell membrane, which could act as a soluble ligand or cleavage could occur after ligand binding and result in signal transduction (Rubin et al., Developmental Biology, 216, 195-209, 1999).

One potential scenario by which transmembrane proteins can fulfill their role as signaling molecules is by a mechanism recently described as regulated intramembrane proteolysis (RIP; reviewed in Brown et al. (2000) Cell 100, 391-98). RIP involves at least two cleavage steps in and at the membrane resulting in a soluble cytoplasmic part, which is translocated to the nucleus where it participates in transcription (Ebinu and Yankner (2002) Neuron 34(4):499-502. RIP is known to control diverse cellular and developmental processes. It is well known, however, that transmembrane proteins can initiate signal transduction by alternative mechanisms, such as ligand binding, receptor binding, and signaling through kinase/phosphatase cascades, etc. Indeed, *Drosophila* ten-m was postulated to modulate the activity of the *Drosophila* pair-rule gene, Odd-paired (opa) protein via a signal transduction cascade (Baumgartner et al., 1994, EMBO J. 13: 3728-3740), although a similarity between the intracellular cleavages of Odz have been linked to those of notch (Dgany and Wides, Biochem J. (2992) 363:633-643). In addition, some evidence show that a portion of Odz might translocate to the nucleus (Bagutti et al. 2003, Kenzelmann et al. 2008). Furthermore, the extracellular domain of mouse Ten m1 was found to exhibit homophilic binding and thereby inititate a signal transduction pathway (Oohashi et al., 1999).

SUMMARY

The present inventors have now surprisingly found that expression as well as protein levels of some teneurins, for example teneurin-4 correlate with tumours, for example brain tumours.

The present invention hence encompasses a method for treating cancer in a subject by inhibiting a teneurin by administering to said subject a therapeutically effective amount of a modulator of said teneurin. In an embodiment, the teneurin is modulated by an inhibitor, for example, a small molecule, an antibody or a siRNA. In some embodiments, the inhibitor decreases or silences the expression of said teneurin, or inhibits the binding of said teneurin to its ligand.

In an embodiment of the invention, the subject is a mammal, in some embodiments, a human subject.

In some embodiments of the invention, the cancer is a cancer of the brain, for example an astrocytoma, a glioblastoma or an oligodendroglioma. In some other embodiments of the invention, the teneurin is teneurin-4. In some particular embodiments, the cancer is a cancer of the brain, for example an astrocytoma, a glioblastoma or an oligodendroglioma, and the teneurin is teneurin-4

Also encompassed by the invention is a siRNA decreasing or silencing the expression of a teneurin, for use as a medicament to treat cancer, or an antibody specifically binding a teneurin, for use as a medicament to treat cancer. In some embodiments, the antibody inhibits the binding of said teneurin to its ligand.

In some embodiments of the invention, the siRNA or antibody of the invention, is used to treat a cancer of the brain, for example an astrocytoma, a glioblastoma or an oligodendroglioma. In yet other embodiments, the siRNA or antibody of the invention is specific for teneurin-4.

The present invention also encompasses a method of diagnosing cancer comprising the step of assessing the level of expression of a teneurin, for example teneurin-4, in a sample from a subject.

An alternative embodiment of the invention relates to a method of diagnosing cancer comprising the step of assessing the concentration of a teneurin in a body fluid. In some embodiments, the body fluid is blood, serum, plasma or cerebro-spinal fluid.

In some embodiments, the cancer to be diagnosed is a cancer of the brain, for example an astrocytoma, a glioblastoma or an oligodendroglioma. In yet other embodiments, the teneurin is teneurin-4. In particular embodiments, the cancer to be diagnosed is a cancer of the brain, for example an astrocytoma, a glioblastoma or an oligodendroglioma. and the teneurin is teneurin-4.

These and other aspects of the present invention should be apparent to those skilled in the art, from the teachings herein.

BRIEF DESCRIPTION OF THE DRAWINGS

The following drawings are illustrative of embodiments of the invention and are not meant to limit the scope of the invention as encompassed by the claims.

DETAILED DESCRIPTION OF THE INVENTION

Figure 1:
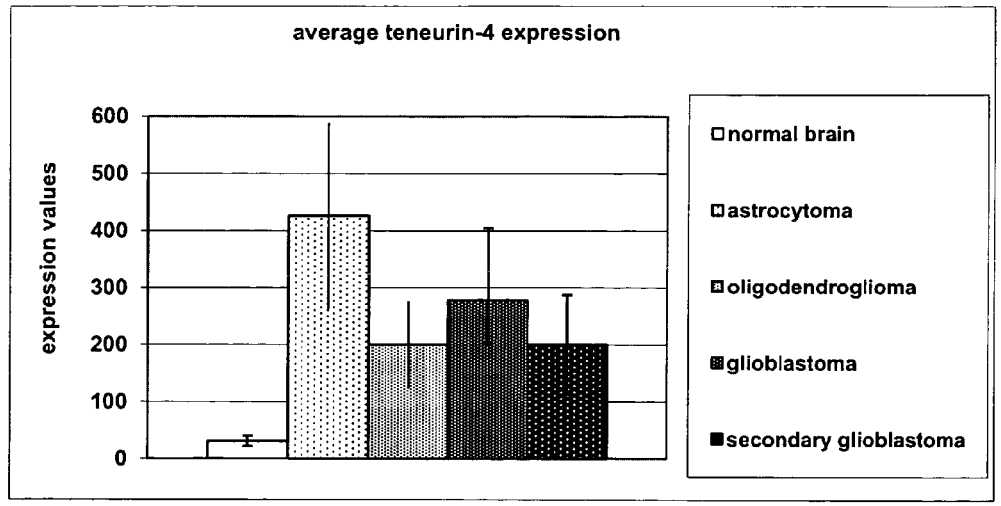
FIG. 1: Average expression level of teneurin-4 in normal brain and brain tumor samples. The average expression levels of teneurin-4 in human normal brain, astrocytoma, oligodendroglioma, glioblastoma and secondary glioblastoma. Error bars indicate the standard deviation. Teneurin-4 is upregulated in all types of brain tumors, 13.7-fold in astrocytoma, 6.3-fold in oligodendroglioma, 8.7-fold in glioblastoma and 6.4-fold in secondary glioblastoma.
Figure 2:
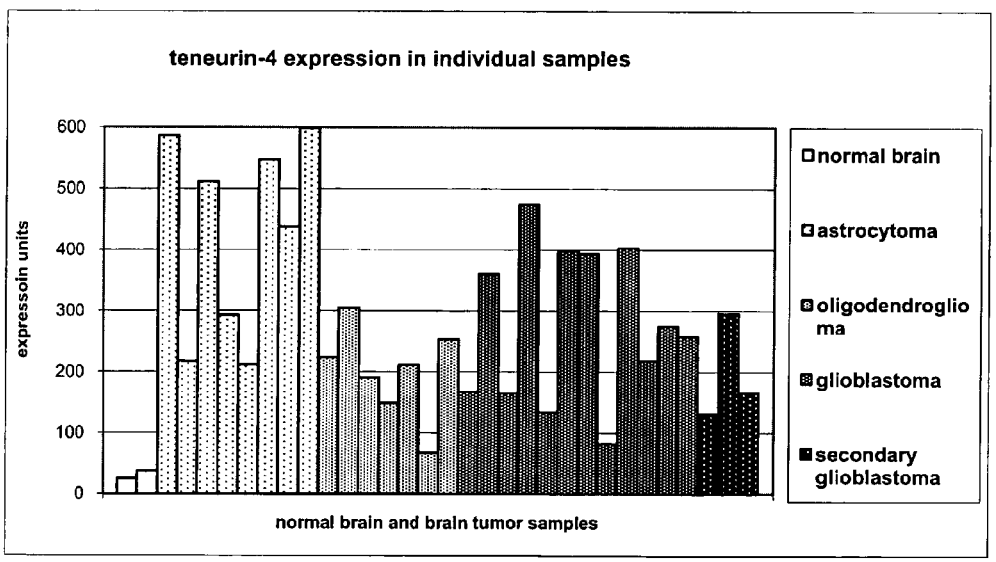
FIG. 2: Expression levels of individual normal brain and brain tumor samples. The expression levels of teneurin-4 in individual samples of human normal brain (n=2), astrocytoma (n=8), oligodendroglioma (n=7), glioblastoma (n=12) and secondary glioblastoma (n=3).
Figure 3:
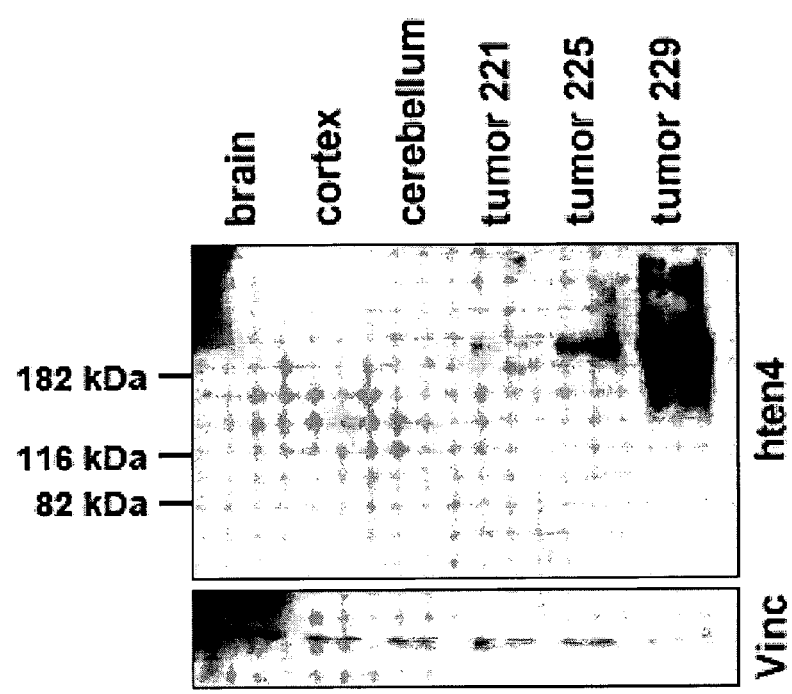
FIG. 3: Comparison teneurin-4 expression normal brain and brain tumors. The teneurin-4 expression levels of three samples of normal brain (total brain, cortex, cerebellum) were compared to three brain tumor samples (glioblastomas 221, 225, 229) with varying teneurin-4 expression levels. Teneurin-4 was absent from normal brain, the brain tumors in contrast express high levels of teneurin-4, for which a molecular weight of >300 kDa is expected.
Figure 4:
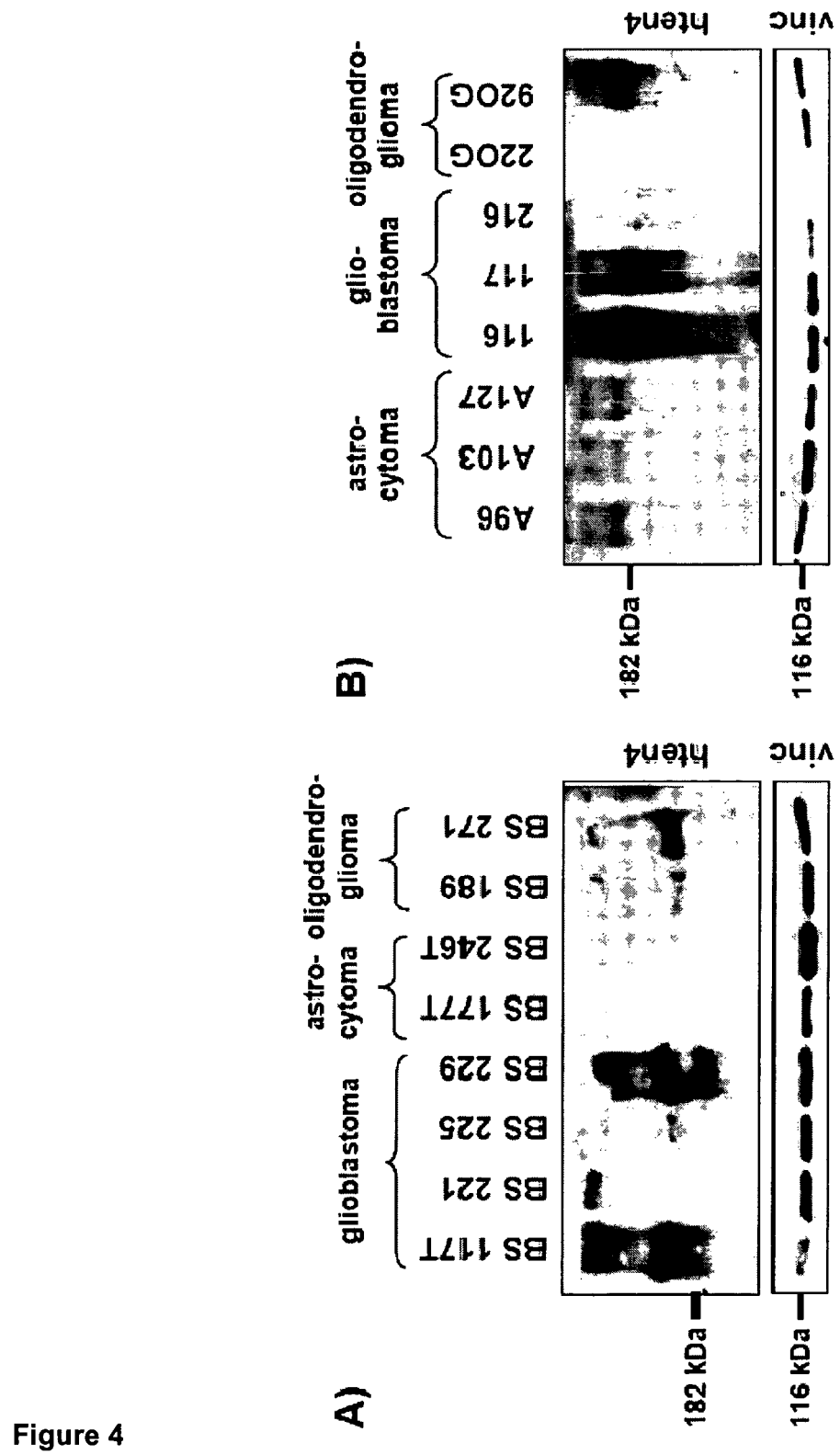
FIG. 4: Western Blot analysis of a panel of brain tumors: Western blot analysis of two panels of brain tumors, wherein the panels are labeled as "A)" and "B)", shows that teneurin-4 expression levels vary between tumors, but teneurin-4 is upregulated in all types of brain tumors (astrocytoma, oligodendroglima, glioblastoma). Vinculin was used as a loading control.
Figure 5:
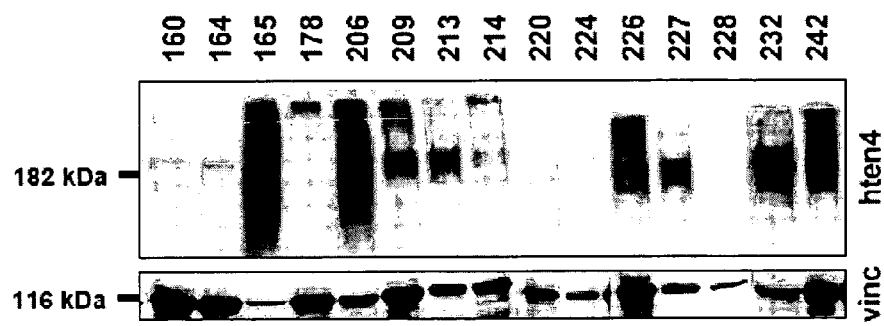
FIG. 5: Western Blot analysis of a panel of glioblastomas. A panel of 15 gliomablastomas was analyzed for teneurin-4 expression. Teneurin-4 is overexpressed in most of the tumors, in some at very high levels. Vinculin was used as a loading control.
Figure 6:
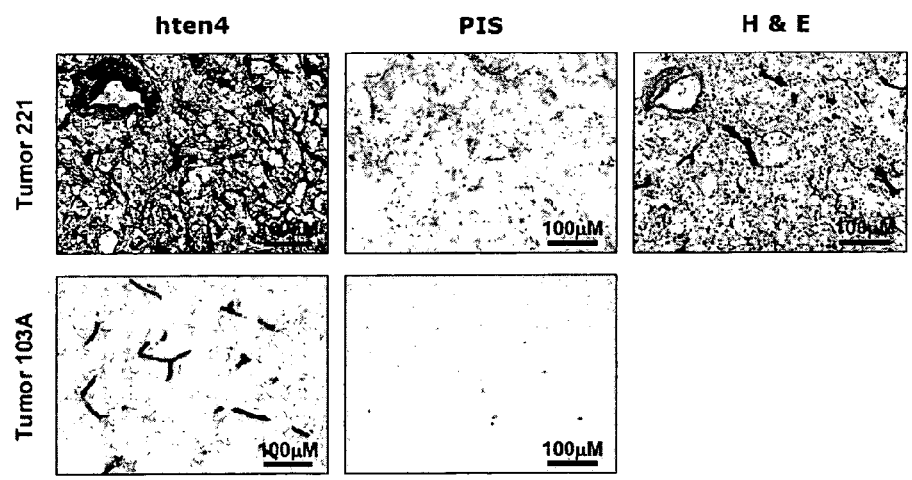
FIG. 6: Immunohistochemistry of brain tumors. Immunohistochemistry shows that in some tumors, the tumor cells express teneurin-4, e.g. tumor 221 (glioblastoma). In other tumors, e.g. 103A (astrocytoma) teneurin-4 staining is restricted to blood vessels. As control, staining with preimmune serum (PIS) was performed as well as H & E staining if enough sections were available.

The present inventors have now surprisingly found that expression as well as protein levels of some teneurins, for example teneurin-4 correlate with tumours, for example brain tumours.

The present invention hence encompasses a method for treating cancer in a subject by inhibiting a teneurin by administering to said subject a therapeutically effective amount of a modulator of said teneurin. In an embodiment, the teneurin is modulated by an inhibitor, for example, a small molecule, an antibody or a siRNA. In some embodiments, the inhibitor decreases or silences the expression of said teneurin, or inhibits the binding of said teneurin to its ligand.

In an embodiment of the invention, the subject is a mammal, in some embodiments, a human subject.

In some embodiments of the invention, the cancer is a cancer of the brain, for example an astrocytoma, a glioblastoma or an oligodendroglioma. In some other embodiments of the invention, the teneurin is teneurin-4. In some particular embodiments, the cancer is a cancer of the brain, for example an astrocytoma, a glioblastoma or an oligodendroglioma, and the teneurin is teneurin-4

Also encompassed by the invention is a siRNA decreasing or silencing the expression of a teneurin, for use as a medicament to treat cancer, or an antibody specifically binding a teneurin, for use as a medicament to treat cancer. In some embodiments, the antibody inhibits the binding of said teneurin to its ligand.

In some embodiments of the invention, the siRNA or antibody of the invention, is used to treat a cancer of the brain, for example an astrocytoma, a glioblastoma or an oligodendroglioma. In yet other embodiments, the siRNA or antibody of the invention is specific for teneurin-4.

The present invention also encompasses a method of diagnosing cancer comprising the step of assessing the level of expression of a teneurin, for example teneurin-4, in a sample from a subject.

An alternative embodiment of the invention relates to a method of diagnosing cancer comprising the step of assessing the concentration of a teneurin in a body fluid. In some embodiments, the body fluid is blood, serum, plasma or cerebro-spinal fluid.

In some embodiments, the cancer to be diagnosed is a cancer of the brain, for example an astrocytoma, a glioblastoma or an oligodendroglioma. In yet other embodiments, the teneurin is teneurin-4. In particular embodiments, the cancer to be diagnosed is a cancer of the brain, for example an astrocytoma, a glioblastoma or an oligodendroglioma. and the teneurin is teneurin-4.

Preferred inhibitors of the invention are small molecules, antibodies and/or siRNA molecules.

These and other aspects of the present invention should be apparent to those skilled in the art, from the teachings herein.

The following definitions are provided to facilitate understanding of certain terms used throughout this specification.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide.

The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. However, a nucleic acid contained in a clone that is a member of a library (e.g., a genomic or cDNA library) that has not been isolated from other members of the library (e.g., in the form of a homogeneous solution containing the clone and other members of the library) or a chromosome removed from a cell or a cell lysate (e.g., a "chromosome spread", as in a karyotype), or a preparation of randomly sheared genomic DNA or a preparation of genomic DNA cut with one or more restriction enzymes is not "isolated" for the purposes of this invention. As discussed further herein, isolated nucleic acid molecules according to the present invention may be produced naturally, recombinantly, or synthetically.

In the present invention, a "secreted" protein refers to a protein capable of being directed to the ER, secretory vesicles, or the extracellular space as a result of a signal sequence, as well as a protein released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

"Polynucleotides" can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotides can be composed of triple-stranded regions comprising RNA or DNA or both RNA and DNA. Polynucleotides may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The expression "polynucleotide encoding a polypeptide" encompasses a polynucleotide which includes only coding sequence for the polypeptide as well as a polynucleotide which includes additional coding and/or non-coding sequence.

"Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1× SSC at about 50 degree C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37 degree C. in a solution comprising 6×SSPE (20×SSPE=3M NaCl; 0.2M NaH2PO4; 0.02M EDTA, pH 7.4), 0.5% SDS, 30% formamide, 100 µg/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The terms "fragment", "derivative" and "analog" when referring to polypeptides means polypeptides which either retain substantially the same biological function or activity as such polypeptides. An analog includes a proprotein which can be activated by cleavage of the proprotein portion to produce an active mature polypeptide.

The term "gene" means the segment of DNA involved in producing a polypeptide chain; it includes regions preceding and following the coding region "leader and trailer" as well as intervening sequences (introns) between individual coding segments (exons).

Polypeptides can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in the polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include, but are not limited to, acetylation, acylation, biotinylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, denivatization by known protecting/blocking groups, disulfide bond formation, demethylation, formation of covalent cross-links, formation of cysteine, formation of pyroglutamate, formylation, gamma-carboxylation, glycosylation, GPI anchor formation, hydroxylation, iodination, linkage to an antibody molecule or other cellular ligand, methylation, myristoylation, oxidation, pegylation, proteolytic processing (e.g., cleavage), phosphorylation, prenylation, racemization, selenoylation, sulfation, transfer-RNA mediated addition of amino acids to proteins such as arginylation, and ubiquitination. (See, for instance, PROTEINS-STRUCTURE AND MOLECULAR PROPERTIES, 2nd Ed., T. E. Creighton, W.H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

A polypeptide fragment "having biological activity" refers to polypeptides exhibiting activity similar, but not necessarily identical to, an activity of the original polypeptide, including mature forms, as measured in a particular biological assay, with or without dose dependency. In the case where dose dependency does exist, it need not be identical to that of the polypeptide, but rather substantially similar to the dose-dependence in a given activity as compared to the original polypeptide (i.e., the candidate polypeptide will exhibit greater activity or not more than about 25-fold less and, in some embodiments, not more than about tenfold less activity, or not more than about three-fold less activity relative to the original polypeptide.)

Species homologs may be isolated and identified by making suitable probes or primers from the sequences provided herein and screening a suitable nucleic acid source for the desired homologue.

"Variant" refers to a polynucleotide or polypeptide differing from the original polynucleotide or polypeptide, but retaining essential properties thereof. Generally, variants are overall closely similar, and, in many regions, identical to the original polynucleotide or polypeptide.

As a practical matter, whether any particular nucleic acid molecule or polypeptide is at least 80%, 85%, 90%, 92%, 95%, 96%, 97%, 98%, 99%, or 100% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. BIosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty-1, Joining Penalty—30, Randomization Group Length=0, Cutoff Score=I, Gap Penalty—5, Gap Size Penalty 0.05, Window Size=500 or the length of the subject nucleotide sequence, whichever is shorter. If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 impaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98%, 99%, or 100% identical to, for instance, the amino acid sequences shown in a sequence or to the amino acid sequence encoded by deposited DNA clone can be determined conventionally using known computer programs. A preferred method for determining, the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty—I, Joining Penalty=20, Randomization Group Length=0, Cutoff Score=1, Window Size=sequence length, Gap Penalty—5, Gap Size Penalty—0.05, Window Size=500 or the length of the subject amino acid sequence, whichever is shorter. If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. Only residue positions outside the N- and C-terminal ends of the subject sequence, as displayed in the FASTDB alignment, which are not matched/aligned with the query sequence are manually corrected for. No other manual corrections are to be made for the purposes of the present invention.

Naturally occurring protein variants are called "allelic variants," and refer to one of several alternate forms of a gene occupying a given locus on a chromosome of an organism. (Genes 11, Lewin, B., ed., John Wiley & Sons, New York (1985).) These allelic variants can vary at either the polynucleotide and/or polypeptide level. Alternatively, non-naturally occurring variants may be produced by mutagenesis techniques or by direct synthesis.

Using known methods of protein engineering and recombinant DNA technology, variants may be generated to improve or alter the characteristics of polypeptides. For instance, one or more amino acids can be deleted from the N-terminus or C-terminus of a secreted protein without substantial loss of biological function. The authors of Ron et al., J. Biol. Chem. 268: 2984-2988 (1993), reported variant KGF proteins having hepanin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., J. Biotechnology 7:199-216 (1988)). Moreover, ample evidence demonstrates that variants often retain a biological activity similar to that of the naturally occurring protein. For example, Gayle and co-workers (J. Biol. Chem. 268:22105-22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[most of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type. Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

In one embodiment where one is assaying for the ability to bind or compete with full-length A teneurin, for example Ten-4, polypeptide for binding to anti-Teneurin, for example Ten-4, antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffasion assays, in situ immunoassays (using colloidal gold, enzyme or radioisotope labels, for example), western blots, precipitation reactions, agglutination assays (e.g., gel agglutination, assays, hemagglutination assays), complement fixation assays, immunofluorescence assays, protein A assays, and immunoelectrophoresis assays, etc. In one embodiment, antibody binding is detected by detecting a label on the primary antibody.

In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Assays described herein and otherwise known in the art may routinely be applied to measure the ability of teneurin, for example Ten-4, polypeptides and fragments, variants derivatives and analogs thereof to elicit teneurin, for example Ten-4-related biological activity (either in vitro or in vivo). For instance, an adhesion, protein binding, or reporter gene activation assay can be used.

The term "epitopes," as used herein, refers to portions of a polypeptide having antigenic or immunogenic activity in an animal, in some embodiments, a mammal, for instance in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immuno specifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

As one of skill in the art will appreciate, and as discussed above, polypeptides comprising an immunogenic or antigenic epitope can be fused to other polypeptide sequences. For example, polypeptides may be fused with the constant domain of immunoglobulins (IgA, IgE, IgG, IgM), or portions thereof (CHI, CH2, CH3, or any combination thereof and portions thereof), or albumin (including but not limited to recombinant albumin (see, e.g., U.S. Pat. No. 5,876,969, issued Mar. 2, 1999, EP Patent 0 413 622, and U.S. Pat. No. 5,766,883, issued Jun. 16, 1998)), resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84-86 (1988).

Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. BIochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers. Additional fusion proteins may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811, 238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998).

Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgGI, IgG2, IgG3, IgG4, IgAI and IgA2) or subclass of immunoglobulin molecule.

In addition, in the context of the present invention, the term "antibody" shall also encompass alternative molecules having the same function of specifically recognizing proteins, e.g. aptamers and/or CDRs grafted onto alternative peptidic or non-peptidic frames.

In some embodiments the antibodies are human antigen-binding antibody fragments and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CHI, CH2, and CH3 domains. Also included in the invention are antigen-binding fragments also comprising any combination of variable region(s) with a hinge region, CHI, CH2, and CH3 domains. The antibodies of the invention may be from any animal origin including birds and mammals. In some embodiments, the antibodies are human, murine (e.g., mouse and rat), donkey, ship rabbit, goat, guinea pig, camel, shark, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al. The antibodies of the present invention may be monospecific, bispecific, trispecific or of greater multi specificity. Multispecific antibodies may be specific for different epitopes of a polypeptide or may be specific for both a polypeptide as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide which they recognize or specifically bind. The epitope(s) or polypeptide portion(s) may be specified as described herein, e.g., by N-terminal and C-terminal positions, by size in contiguous amino acid residues.

Antibodies may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%. less than 55%, and less than 50% identity (as calculated using methods known in the art and described herein) to a polypeptide are also included in the present invention.

Antibodies may also be described or specified in terms of their binding affinity to a polypeptide Antibodies may act as agonists or antagonists of the recognised polypeptides. The invention also features receptor-specific antibodies which do not prevent ligand binding but prevent receptor activation. Receptor activation (i.e., signalling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are antibodies which bind the ligand, thereby preventing receptor activation, but do not prevent the ligand from binding the receptor. The antibodies may be specified as agonists, antagonists or inverse agonists for biological activities comprising the specific biological activities of the peptides disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4):1786-1794 (1998); Zhu et al., Cancer Res. 58(15):3209-3214 (1998); Yoon et al., J. Immunol. 160 (7):3170-3179 (1998); Prat et al., J. Cell. Sci. III(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9):1153-1167 (1998); Bartunek et al., Cytokine 8(I):14-20 (1996).

As discussed in more detail below, the antibodies may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396, 387.

The antibodies as defined for the present invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen.

Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvurn*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

For example, the antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. As described in these references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax. et al., BioTechniques 12(6):864-869 (1992); and Sawai et al., AJRI 34:26-34 (1995); and Better et al., Science 240:1041-1043 (1988).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816397. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, and/or improve, antigen binding. These framework substitutions are identified by methods well known in the art, e.g., by modelling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988).) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592, 106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immurnol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Furthermore, antibodies can be utilized to generate anti-idiotype antibodies that "mimic" polypeptides using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization. and/or binding of a polypeptide to a ligand can be used to generate anti-idiotypes that "mimic" the polypeptide multimerization. and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide and/or to bind its ligands/receptors, and thereby block its biological activity.

Polynucleotides encoding antibodies, comprising a nucleotide sequence encoding an antibody are also encompassed. These polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

The amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and in some embodiments, human framework regions (see, e.g., Chothia et al., J. Mol. Biol. 278: 457-479 (1998) for a listing of human framework regions). In some embodiments, the polynucleotide generated by the combination of the framework regions and CDRs encodes an antibody that specifically binds a polypeptide. In some embodiments, as discussed supra, one or more amino acid substitutions may be made within the framework regions, and, in some embodiments, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polymicleotide are encompassed by the present description and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

The present invention encompasses antibodies recombinantly fused or chemically conjugated (including both covalently and non-covalently conjugations) to a polypeptide (or portion thereof, in some embodiments, at least 10, 20, 30, 40, 50, 60, 70, 80, 90 or 100 amino acids of the polypeptide) to generate fusion proteins. The fusion does not necessarily need to be direct, but may occur through linker sequences. The antibodies may be specific for antigens other than polypeptides (or portion thereof, in some embodiments, at least 10, 20, 30, 40, 50, 60, 70, 80, 90 or 100 amino acids of the polypeptide).

Further, an antibody or fragment thereof may be conjugated to a therapeutic moiety. The conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, B-interferon, nerve growth factor, platelet derived growth factor, tissue plasminogen activator, an apoptotic agent, e.g., TNF-alpha, TNF-beta, AIM I (See, International Publication No. WO 97/33899), AIM 11 (See, International Publication No. WO 97/34911), Fas Ligand (Takahashi et al., Int. Immunol., 6:1567-1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-I"), interleukin-2 ("IL-2"), interleukin-6 ("IL-6"), granulocyte macrophage colony stimulating factor ("GM-CSF"), granulocyte colony stimulating factor ("G-CSF"), or other growth factors. Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980.

The present invention is also directed to antibody-based therapies which involve administering antibodies of the invention to an animal, in some embodiments, a mammal, for example a human, patient to treat cancer. Therapeutic compounds include, but are not limited to, antibodies (including fragments, analogs and derivatives thereof as described herein) and nucleic acids encoding antibodies of the invention (including fragments, analogs and derivatives thereof and anti-idiotypic antibodies as described herein). Antibodies of the invention may be provided in pharmaceutically acceptable compositions as known in the art or as described herein.

The invention also provides methods for treating cancer in a subject by inhibiting a teneurin, for example Ten-4, by administration to the subject of an effective amount of an inhibitory compound or pharmaceutical composition comprising such inhibitory compound. In some embodiments, said inhibitory compound is an antibody or an siRNA. In a preferred aspect, the compound is substantially purified (e.g., substantially free from substances that limit its effect or produce undesired side-effects). The subject is in some embodiments, an animal, including but not limited to animals such as cows, pigs, horses, chickens, cats, dogs, camels, etc., and is in some embodiments, a mammal, for example human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.) In yet another embodiment, the compound or composition can be delivered in a controlled release system. In one embodiment, a pump may be used (see Langer, supra; Sefton, CRC Crit. Ref, Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

The present invention also provides pharmaceutical compositions for use in the treatment of cancer by inhibiting a teneurin, for example Ten-4. Such compositions comprise a therapeutically effective amount of an inhibitory compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, tale, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, in some embodiments, in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anaesthetic such as lidocaine to ease pain at the site of the injection.

Generally, the ingredients are supplied either separately or mixed together in unit dosage form, for example, as a dry lyophilized powder or water free concentrate in a hermetically sealed container such as an ampoule or sachet indicating the quantity of active agent.

Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms.

Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. The amount of the compound which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

Effective doses may be extrapolated from dose-response curves derived from in vitro or animal model test systems.

For antibodies, the dosage administered to a patient is typically 0.1 mg/kg to 100 mg/kg of the patient's body weight. In some embodiments, the dosage administered to a patient is between 0.1 mg/kg and 20 mg/kg of the patient's body weight, for example 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

Also encompassed is a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The antibodies as encompassed herein may also be chemically modified derivatives which may provide additional advantages such as increased solubility, stability and circulating time of the polypeptide, or decreased immunogenicity (see U.S. Pat. No. 4,179,337). The chemical moieties for derivatisation may be selected from water soluble polymers such as polyethylene glycol, ethylene glycol/propylene glycol copolymers, carboxymethyl cellulose, dextran, polyvinyl alcohol and the like. The antibodies may be modified at random positions within the molecule, or at predetermined positions within the molecule and may include one, two, three or more attached chemical moieties. The polymer may be of any molecular weight, and may be branched or unbranched. For polyethylene glycol, the preferred molecular weight is between about 1 kDa and about 100000 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,600, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999). The polyethylene glycol molecules (or other chemical moieties) should be attached to the protein with consideration of effects on functional or antigenic domains of the protein. There are a number of attachment methods available to those skilled in the art, e.g., EP 0 401 384 (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group. As suggested above, polyethylene glycol may be attached to proteins via linkage to any of a number of amino acid residues. For example, polyethylene glycol can be linked to proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein. As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. No. 4,002,531; U.S. Pat. No. 5,349,052; WO 95/06058; and WO 98/32466.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and cerebro-spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

"RNAi" is the process of sequence specific post-transcriptional gene silencing in animals and plants. It uses small interfering RNA molecules (siRNA) that are double-stranded and homologous in sequence to the silenced (target) gene. Hence, sequence specific binding of the siRNA molecule with mRNAs produced by transcription of the target gene allows very specific targeted knockdown' of gene expression.

"siRNA" or "small-interfering ribonucleic acid" according to the invention has the meanings known in the art, including the following aspects. The siRNA consists of two strands of ribonucleotides which hybridize along a complementary region under physiological conditions. The strands are normally separate. Because of the two strands have separate roles in a cell, one strand is called the "anti-sense" strand, also known as the "guide" sequence, and is used in the functioning RISC complex to guide it to the correct mRNA for cleavage. This use of "anti-sense", because it relates to an RNA compound, is different from the antisense target DNA compounds referred to elsewhere in this specification. The other strand is known as the "anti-guide" sequence and because it contains the same sequence of nucleotides as the target sequence, it is also known as the sense strand. The strands may be joined by a molecular linker in certain embodiments. The individual ribonucleotides may be unmodified naturally occurring ribonucleotides, unmodified naturally occurring deoxyribonucleotides or they may be chemically modified or synthetic as described elsewhere herein.

In some embodiments, the siRNA molecule is substantially identical with at least a region of the coding sequence of the target gene to enable down-regulation of the gene. In some embodiments, the degree of identity between the sequence of the siRNA molecule and the targeted region of the gene is at least 60% sequence identity, in some embodiments at least 75% sequence identity, for instance at least 85% identity, 90% identity, at least 95% identity, at least 97%, or at least 99% identity.

Calculation of percentage identities between different amino acid/polypeptide/nucleic acid sequences may be carried out as follows. A multiple alignment is first generated by the ClustalX program (pairwise parameters: gap opening 10.0, gap extension 0.1, protein matrix Gonnet 250, DNA matrix IUB; multiple parameters: gap opening 10.0, gap extension 0.2, delay divergent sequences 30%, DNA transition weight 0.5, negative matrix off, protein matrix gonnet series, DNA weight IUB; Protein gap parameters, residue-specific penalties on, hydrophilic penalties on, hydrophilic residues GPSNDQERK, gap separation distance 4, end gap separation off). The percentage identity is then calculated from the multiple alignment as (N/T)*100, where N is the number of positions at which the two sequences share an identical residue, and T is the total number of positions compared. Alternatively, percentage identity can be calculated as (N/S)*100 where S is the length of the shorter sequence being compared. The amino acid/polypeptide/nucleic acid sequences may be synthesised de novo, or may be native amino acid/polypeptide/nucleic acid sequence, or a derivative thereof. A substantially similar nucleotide sequence will be encoded by a sequence which hybridizes to any of the nucleic acid sequences referred to herein or their complements under stringent conditions. By stringent conditions, we mean the nucleotide hybridises to filter-bound DNA or RNA in 6× sodium chloride/sodium citrate (SSC) at approximately 45° C. followed by at least one wash in 0.2×SSC/0.1% SDS at approximately 5-65° C. Alternatively, a substantially similar polypeptide may differ by at least 1, but less than 5, 10, 20, 50 or 100 amino acids from the peptide sequences according to the present invention Due to the degeneracy of the genetic code, it is clear that any nucleic acid sequence could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequences which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine; large non-polar, hydrophobic amino acids include phenylalanine, tryptophan and tyrosine; the polar neutral amino acids include serine, threonine, cysteine, asparagine and glutamine; the positively charged (basic) amino acids include lysine, arginine and histidine; and the negatively charged (acidic) amino acids include aspartic acid and glutamic acid.

The accurate alignment of protein or DNA sequences is a complex process, which has been investigated in detail by a number of researchers. Of particular importance is the trade-off between optimal matching of sequences and the introduction of gaps to obtain such a match. In the case of proteins, the means by which matches are scored is also of significance. The family of PAM matrices (e.g., Dayhoff, M. et al., 1978, Atlas of protein sequence and structure, Natl. Biomed. Res. Found.) and BLOSUM matrices quantify the nature and likelihood of conservative substitutions and are used in multiple alignment algorithms, although other, equally applicable matrices will be known to those skilled in the art. The popular multiple alignment program ClustalW, and its windows version ClustalX (Thompson et al., 1994, Nucleic Acids Research, 22, 4673-4680; Thompson et al., 1997, Nucleic Acids Research, 24, 4876-4882) are efficient ways to generate multiple alignments of proteins and DNA.

Frequently, automatically generated alignments require manual alignment, exploiting the trained user's knowledge of the protein family being studied, e.g., biological knowledge of key conserved sites. One such alignment editor programs is Align (http://www.gwdg.de/dhepper/download/; Hepperle, D., 2001: Multicolor Sequence Alignment Editor. Institute of Freshwater Ecology and Inland Fisheries, 16775 Stechlin, Germany), although others, such as JalView or Cinema are also suitable.

Calculation of percentage identities between proteins occurs during the generation of multiple alignments by Clustal. However, these values need to be recalculated if the alignment has been manually improved, or for the deliberate comparison of two sequences. Programs that calculate this value for pairs of protein sequences within an alignment include PROTDIST within the PHYLIP phylogeny package (Felsenstein; http://evolution.gs.washington.edu/phylip.html) using the "Similarity Table" option as the model for amino acid substitution (P). For DNA/RNA, an identical option exists within the DNADIST program of PHYLIP.

The dsRNA molecules in accordance with the present invention comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. In an embodiment, the RNA molecules of the present invention specifically target one given gene. In order to only target the desired mRNA, the siRNA reagent may have 100% homology to the target mRNA and at least 2 mismatched nucleotides to all other genes present in the cell or organism. Methods to analyze and identify siRNAs with sufficient sequence identity in order to effectively inhibit expression of a specific target sequence are known in the art. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BEST-FIT software program using default parameters (e.g., University of Wisconsin Genetic Computing Group).

The length of the region of the siRNA complementary to the target, in accordance with the present invention, may be from 10 to 100 nucleotides, 12 to 25 nucleotides, 14 to 22 nucleotides or 15, 16, 17 or 18 nucleotides. Where there are mismatches to the corresponding target region, the length of the complementary region is generally required to be somewhat longer. In a preferred embodiment, the inhibitor is a siRNA molecule and comprises between approximately 5 bp and 50 bp, in some embodiments, between 10 bp and 35 bp, or between 15 bp and 30 bp, for instance between 18 bp and 25 bp. In some embodiments, the siRNA molecule comprises more than 20 and less than 23 bp.

Because the siRNA may carry overhanging ends (which may or may not be complementary to the target), or additional nucleotides complementary to itself but not the target gene, the total length of each separate strand of siRNA may be 10 to 100 nucleotides, 15 to 49 nucleotides, 17 to 30 nucleotides or 19 to 25 nucleotides.

The phrase "each strand is 49 nucleotides or less" means the total number of consecutive nucleotides in the strand, including all modified or unmodified nucleotides, but not including any chemical moieties which may be added to the 3' or 5' end of the strand. Short chemical moieties inserted into the strand are not counted, but a chemical linker designed to join two separate strands is not considered to create consecutive nucleotides.

The phrase "a 1 to 6 nucleotide overhang on at least one of the 5' end or 3' end" refers to the architecture of the complementary siRNA that forms from two separate strands under physiological conditions. If the terminal nucleotides are part of the double-stranded region of the siRNA, the siRNA is considered blunt ended. If one or more nucleotides are unpaired on an end, an overhang is created. The overhang length is measured by the number of overhanging nucleotides. The overhanging nucleotides can be either on the 5' end or 3' end of either strand.

The siRNA according to the present invention display a high in vivo stability and may be particularly suitable for oral delivery by including at least one modified nucleotide in at least one of the strands. Thus the siRNA according to the present invention contains at least one modified or non-natural ribonucleotide. A lengthy description of many known chemical modifications are set out in published PCT patent application WO 200370918. Suitable modifications for delivery include chemical modifications can be selected from among:
 a) a 3' cap;
 b) a 5' cap,
 c) a modified internucleoside linkage; or
 d) a modified sugar or base moiety.

Suitable modifications include, but are not limited to modifications to the sugar moiety (i.e. the 2' position of the sugar moiety, such as for instance 2'-O-(2-methoxyethyl) or 2'-MOE) (Martin et al., Helv. Chim. Acta, 1995, 78, 486-504) i.e., an alkoxyalkoxy group) or the base moiety (i.e. a non-natural or modified base which maintains ability to pair with another specific base in an alternate nucleotide chain). Other modifications include so-called 'backbone' modifications including, but not limited to, replacing the phosphoester group (connecting adjacent ribonucleotides) with for instance phosphorothioates, chiral phosphorothioates or phosphorodithioates.

End modifications sometimes referred to herein as 3' caps or 5' caps may be of significance. Caps may consist of simply adding additional nucleotides, such as "T-T" which has been found to confer stability on a siRNA. Caps may consist of more complex chemistries which are known to those skilled in the art.

Design of a suitable siRNA molecule is a complicated process, and involves very carefully analysing the sequence of the target mRNA molecule. On exemplary method for the design of siRNA is illustrated in WO2005/059132. Then, using considerable inventive endeavour, the inventors have to choose a defined sequence of siRNA which has a certain composition of nucleotide bases, which would have the required affinity and also stability to cause the RNA interference.

The siRNA molecule may be either synthesised de novo, or produced by a micro-organism. For example, the siRNA molecule may be produced by bacteria, for example, E. coli. Methods for the synthesis of siRNA, including siRNA containing at least one modified or non-natural ribonucleotides are well known and readily available to those of skill in the art. For example, a variety of synthetic chemistries are set out in published PCT patent applications WO2005021749 and WO200370918. The reaction may be carried out in solution or, in some embodiments, on solid phase or by using polymer supported reagents, followed by combining the synthesized RNA strands under conditions, wherein a siRNA molecule is formed, which is capable of mediating RNAi.

It should be appreciated that siNAs (small interfering nucleic acids) may comprise uracil (siRNA) or thyrimidine (siDNA). Accordingly the nucleotides U and T, as referred to above, may be interchanged. However it is preferred that siRNA is used.

Gene-silencing molecules, i.e. inhibitors, used according to the invention are in some embodiments, nucleic acids (e.g. siRNA or antisense or ribozymes). Such molecules may (but not necessarily) be ones, which become incorporated in the DNA of cells of the subject being treated. Undifferentiated cells may be stably transformed with the gene-silencing molecule leading to the production of genetically modified daughter cells (in which case regulation of expression in the subject may be required, e.g. with specific transcription factors, or gene activators).

The gene-silencing molecule may be either synthesised de novo, and introduced in sufficient amounts to induce gene-silencing (e.g. by RNA interference) in the target cell. Alternatively, the molecule may be produced by a micro-organism, for example, E. coli, and then introduced in sufficient amounts to induce gene silencing in the target cell.

The molecule may be produced by a vector harbouring a nucleic acid that encodes the gene-silencing sequence. The vector may comprise elements capable of controlling and/or enhancing expression of the nucleic acid. The vector may be a recombinant vector. The vector may for example comprise plasmid, cosmid, phage, or virus DNA. In addition to, or instead of using the vector to synthesise the gene-silencing molecule, the vector may be used as a delivery system for transforming a target cell with the gene silencing sequence.

The recombinant vector may also include other functional elements. For instance, recombinant vectors can be designed such that the vector will autonomously replicate in the target cell. In this case, elements that induce nucleic acid replication may be required in the recombinant vector. Alternatively, the recombinant vector may be designed such that the vector and recombinant nucleic acid molecule integrates into the genome of a target cell. In this case nucleic acid sequences, which favour targeted integration (e.g. by homologous recombination) are desirable. Recombinant vectors may also have DNA coding for genes that may be used as selectable markers in the cloning process.

The recombinant vector may also comprise a promoter or regulator or enhancer to control expression of the nucleic acid as required. Tissue specific promoter/enhancer elements may be used to regulate expression of the nucleic acid in specific cell types, for example, endothelial cells. The promoter may be constitutive or inducible.

Alternatively, the gene silencing molecule may be administered to a target cell or tissue in a subject with or without it being incorporated in a vector. For instance, the molecule may be incorporated within a liposome or virus particle (e.g. a retrovirus, herpes virus, pox virus, vaccina virus, adenovirus, lentivirus and the like).

Alternatively a "naked" siRNA or antisense molecule may be inserted into a subjects cells by a suitable means e.g. direct endocytotic uptake.

The gene silencing molecule may also be transferred to the cells of a subject to be treated by either transfection, infection, microinjection, cell fusion, protoplast fusion or ballistic bombardment. For example, transfer may be by: ballistic transfection with coated gold particles; liposomes containing a siNA molecule; viral vectors comprising a gene silencing sequence or means of providing direct nucleic acid uptake (e.g. endocytosis) by application of the gene silencing molecule directly.

In a preferred embodiment of the present invention siNA molecules may be delivered to a target cell (whether in a vector or "naked") and may then rely upon the host cell to be replicated and thereby reach therapeutically effective levels. When this is the case the siNA is in some embodiments, incorporated in an expression cassette that will enable the siNA to be transcribed in the cell and then interfere with translation (by inducing destruction of the endogenous mRNA coding the targeted gene product).

Inhibitors according to any embodiment of the present invention may be used in a monotherapy (e.g. use of siRNAs alone). However it will be appreciated that the inhibitors may be used as an adjunct, or in combination with other therapies.

The inhibitors of teneurin, for example inhibitor of Ten-4, may be contained within compositions having a number of different forms depending, in particular on the manner in which the composition is to be used. Thus, for example, the composition may be in the form of a capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given, and in some embodiments, enables delivery of the inhibitor to the target site.

The inhibitors of Teneurin, for example inhibitor of Ten-4, may be used in a number of ways.

For instance, systemic administration may be required in which case the compound may be contained within a composition that may, for example, be administered by injection into the blood stream. Injections may be intravenous (bolus or infusion), subcutaneous, intramuscular or a direct injection into the target tissue (e.g. an intraventricular injection-when used in the brain). The inhibitors may also be administered by inhalation (e.g. intranasally) or even orally (if appropriate).

The inhibitors of the invention may also be incorporated within a slow or delayed release device. Such devices may, for example, be inserted at the site of a tumour, and the molecule may be released over weeks or months. Such devices may be particularly advantageous when long term treatment with an inhibitor of a teneurin, for example an inhibitor of Ten-4, is required and which would normally require frequent administration (e.g. at least daily injection).

It will be appreciated that the amount of an inhibitor that is required is determined by its biological activity and bioavailability which in turn depends on the mode of administration, the physicochemical properties of the molecule employed and whether it is being used as a monotherapy or in a combined therapy. The frequency of administration will also be influenced by the above-mentioned factors and particularly the half-life of the inhibitor within the subject being treated.

Optimal dosages to be administered may be determined by those skilled in the art, and will vary with the particular inhibitor in use, the strength of the preparation, and the mode of administration.

Additional factors depending on the particular subject being treated will result in a need to adjust dosages, including subject age, weight, gender, diet, and time of administration.

When the inhibitor is a nucleic acid conventional molecular biology techniques (vector transfer, liposome transfer, ballistic bombardment etc) may be used to deliver the inhibitor to the target tissue.

Known procedures, such as those conventionally employed by the pharmaceutical industry (e.g. in vivo experimentation, clinical trials, etc.), may be used to establish specific formulations for use according to the invention and precise therapeutic regimes (such as daily doses of the gene silencing molecule and the frequency of administration).

Generally, a daily dose of between 0.01 µg/kg of body weight and 0.5 g/kg of body weight of an inhibitor of A teneurin, for example Ten-4, may be used for the treatment of cancer in the subject, depending upon which specific inhibitor is used. When the inhibitor is an siRNA molecule, the daily dose may be between 1 pg/kg of body weight and 100 mg/kg of body weight, in some embodiments, between approximately 10 pg/kg and 10 mg/kg, or between about 50 pg/kg and 1 mg/kg.

When the inhibitor (e.g. siNA) is delivered to a cell, daily doses may be given as a single administration (e.g. a single daily injection).

Various assays are known in the art to test dsRNA for its ability to mediate RNAi (see for instance Elbashir et al., Methods 26 (2002), 199-213). The effect of the dsRNA according to the present invention on gene expression will typically result in expression of the target gene being inhibited by at least 10%, 33%, 50%, 90%, 95% or 99% when compared to a cell not treated with the RNA molecules according to the present invention.

Similarly, various assays are well-known in the art to test antibodies for their ability to inhibit the biological activity of their specific targets. The effect of the use of an antibody according to the present invention will typically result in biological activity of their specific target being inhibited by at least 10%, 33%, 50%, 90%, 95% or 99% when compared to a control not treated with the antibody.

The term "cancer" refers to a group of diseases in which cells are aggressive (grow and divide without respect to normal limits), invasive (invade and destroy adjacent tissues), and sometimes metastatic (spread to other locations in the body). These three malignant properties of cancers differentiate them from benign tumors, which are self-limited in their growth and don't invade or metastasize (although some benign tumor types are capable of becoming malignant). A particular type of cancer, preferred in the context of the present invention is a cancer forming solid tumours. Such cancer forming solid tumours can be breast cancer, prostate carcinoma or oral squamous carcinoma. Other cancer forming solid tumours for which the methods and inhibitors of the invention would be well suited can be selected from the group consisting of adrenal cortical carcinomas, angiomatoid fibrous histiocytomas (AFH), squamous cell bladder carcinomas, urothelial carcinomas, bone tumours, e.g. adamantinomas, aneurysmal bone cysts, chondroblastomas, chondromas, chondromyxoid fibromas, chondrosarcomas, fibrous dysplasias of the bone, giant cell tumours, osteochondromas or osteosarcomas, breast tumours, e.g. secretory ductal carcinomas, chordomas, clear cell hidradenomas of the skin (CCH), colorectal adenocarcinomas, carcinomas of the gallbladder and extrahepatic bile ducts, combined hepatocellular and cholangiocarcinomas, fibrogenesis imperfecta ossium, pleomorphic salivary gland adenomas head and neck squamous cell carcinomas, chromophobe renal cell carcinomas, clear cell renal cell carcinomas, nephroblastomas (Wilms tumor), papillary renal cell carcinomas, primary renal ASPSCR1-TFE3 t(X; 17)(p11; q25) tumors, renal cell carcinomas, laryngeal squamous cell carcinomas, liver adenomas, hepatoblastomas, hepatocellular carcinomas, non-small cell lung carcinomas, small cell lung cancers, malignant melanoma of soft parts, medulloblastomas, meningiomas, neuroblastomas, astrocytic tumours, ependymomas, peripheral nerve sheath tumours, neuroendocrine tumours, e.g. phaeochromocytomas, neurofibromas, oral squamous cell carcinomas, ovarian tumours, e.g. epithelial ovarian tumours, germ cell tumours or sex cord-stromal tumours, pericytomas, pituitary adenomas, posterior uveal melanomas, rhabdoid tumours, skin melanomas, cutaneous benign fibrous histiocytomas, intravenous leiomyomatosis, aggressive angiomyxomas, liposarcomas, myxoid liposarcomas, low grade fibromyxoid sarcomas, soft tissue leiomyosarcomas, biphasic synovial sarcomas, soft tissue chondromas, alveolar soft part sarcomas, clear cell sarcomas, desmoplastic small round cell tumours, elastofibromas, Ewing's tumours, extraskeletal myxoid chondrosarcomas, inflammatory myofibroblastic tumours, lipoblastomas, lipoma, benign lipomatous tumours, liposarcomas, malignant lipomatous tumours, malignant myoepitheliomas, rhabdomyosarcomas, synovial sarcomas, squamous cell cancers, subungual exostosis, germ cell tumours in the testis, spermatocytic seminomas, anaplastic (undifferentiated) carcinomas, oncocytic tumours, papillary carcinomas, carcinomas of the cervix, endometrial carcinomas, leiomyoma as well as vulva and/or vagina tumours. In some embodiments, the cancer is a brain cancer, or brain tumor, for example an astrocytoma, a glioblastoma or an oligodendroglioma.

The term "teneurin" refers to a family of are transmembrane proteins. Teneurins are highly conserved between *Drosophila, C. elegans* and vertebrates. In each species they are expressed by a subset of neurons as well as at sites of pattern formation and morphogenesis. In *Drosophila*, a teneurin known as ten-m or Odz is a pair-rule gene, and its expression is required for normal development. The knockdown of teneurin (ten-1) expression in *C. elegans* with RNAi leads to abnormal neuronal pathfinding and abnormal development of the gonads. The intracellular domain of some, if not all, teneurins can be cleaved and transported to the cell nucleus, where it proposed to act as a transcription factor. A peptide derived from the terminus of the extracellular domain shares structural homology with certain neuropeptides. There are four teneurin genes in vertebrates named teneurin-1, teneurin-2, teneurin-3 or teneurin-4. Other names found in the literature include Odz-1 through -4 and Tenm-1 through -4.

The term "teneurin-4" or "Ten-4", also known as Doc4, FLJ99165, KIAA1302, TNM4, Ten-M4, Ten-m4, tenscin-M4, odz4 or protein Odd Oz/ten-m homolog 4, refers to a member of the teneurin family. The Entrez GeneID for Ten-4 is: 26011.

The present invention also provides a method of screening compounds to identify those which might be useful for treating cancer in a subject by modulating the expression or the protein levels of a teneurin, for example the levels of Ten-4, as well as the so-identified compounds.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

EXAMPLES

Microarray Analysis of Brain Tumors

Total RNA was extracted from the primary tumor samples using Trizol™ reagent, According to Manufacturer's instructions, and resuspended in diethylpyrocarbonate (DEPC) treated water. Total RNA was further purified using the RNeasy™ kit and following the protocol for Total RNA cleanup. RNA was then amplified and labeled using the Affymetrix 2-cycle amplification protocol as per manufacturer's instructions (Affymetrix). Samples were hybridized to Affymetrix U133v2.0 GeneChips and scanned using an Affymetrix GeneChip scanner as per manufacturer's instructions. Expression values were estimated using the GC-RMA implementation found in Genedata's Refiner 4.1 (Genedata, Basel, Switzerland) package. Data-mining and visualization was performed using Genedata's Analyst 4.1 package. All samples were quantile normalized and median scaled to correct for minor variations in their expression distributions.

Production of Antibodies Against Human Teneurin-4

RT-PCR was performed on human brain RNA using the Superscript RT-PCR kit (Invitrogen) and oligodT primers. The obtained cDNA was subsequently used as a template for PCR amplification of human teneurin-4 sequences. A recombinant fusion protein between the Tenascin-C (TNC) signal peptide and the human teneurin-4 EGF-like repeats was generated. The following primers were used:
TNC/hten4 EGF fw: CGGCAGACTGGGCTCAAT-GAGTCGGTGGATAACTGC (SEQ ID NO:1), TNC/hten4 EGF rev: GCAGTTATCCACCGACTCATTGAGC-CCAGTCTCCCG (SEQ ID NO:2) and hten4 EGF rev: TAGTGCGGCCGCTTAGTGATGGTGATG-GTGATGATCATTGTCTTTGCTGTCACC (SEQ ID NO:3) containing a HIS tag and Not/site. The resulting PCR fragment was cloned using HindIII and NotI, sequenced and transfected into 293T EBNA cells. Expression and secretion of the recombinant protein in 293T-EBNA cells was verified by western blot analysis of cell lysates and cell culture medium using the penta-HIS antibody (Qiagen). Cells stably expressing the TNC/hten4 EGF protein were selected with G418 for the EBNA-plasmid (Promega) and Puromycin for the pCEP plasmid (Sigma). These cells were finally grown in 0.3% FCS in triple flasks (Nunc) to produce and secrete the TNC/cten4 EGF protein. Subsequently, the recombinant protein was purified from the tissue culture medium and sent for injection into rabbits to generate polyclonal antibodies (RCC). The antibodies were first tested on recombinant protein, and subsequently on cell and tissue lysates.

Western Blot Analysis of Brain Tumors

Protein lysates were prepared from pieces of frozen tumor material that was obtained from the Merlo lab at the University hospital, Basel. RIPA-buffer was added to the tumor pieces and they were homogenized by using a small pestle. The lysates were clarified by centrifugation and the protein concentration determined by a Bradford Assay. Normal brain protein samples were purchased from BioChain, including one sample of total brain (P1234035, age 71 Lot No A908046), cerebral cortex (P1234042, age 77, Lot No B107064) and cerebellum (P1234040, age 66, Lot No B109120). The samples were analyzed on a 7.5% Polyacrylamid-gel, blotted for 2 h using a semi-dry system and stained with amidoblack to verify the amount of protein on the membrane. HRP-labeled secondary antibody was used at a dilution of 1:10'000 and the signal detected by Super Signal (Pierce). As a loading control mouse monoclonal vinculin antibodies (Sigma) were used.

Immunohistochemistry of Brain Tumors

Frozen sections of brain tumors were obtained by the Merlo lab at the University Hospital, Basel. The sections were stained with the Ventana Automated Staining module using the standard IHC protocol with the following parameters: No pretreatment, 4 min AB-block, primary antibody incubation 60 min, secondary anti-rabbit incubation 32 min, Hematoxylin counterstain. Both hten4 EGFA and hten4 EGFB antibodies were used 1:1000 and resulted in similar staining, and subsequently only hten4 EGFA was used. A control using the preimmune serum was performed in parallel, and if enough sections were available also H&E staining. H&E Staining Procedure: Thaw 20' at RT, 30" dH2O, 1×2' Hematoxylin, rinse dH2O, 5' tap water, 12×dip in acid ethanol, 2×1' tap water, 2' H2O, 30' Eosin, 2×2" 95% EtOH, 2×2" 100% EtOH, 2×5' Histoclear. Stained sections were coverslipped using the Histoclear kit, dried for at least 30 min and viewed on an Olympus Eclipse E600 microscope. Images were acquired using the Image Access software.

REFERENCES

1. Cong F, Schweizer L, Varmus H: Casein kinase I epsilon modulates the signaling specificities of dishevelled. Mol Cell Biol 2004, 24:2000-2011.
2. Willert K, Brink M, Wodarz A, Varmus H, Nusse R: Casein kinase 2 associates with and phosphorylates dishevelled. Embo J 1997, 16:3089-3096.
3. Kuhl M, Geis K, Sheldahl L C, Pukrop T, Moon R T, Wedlich D: Antagonistic regulation of convergent extension movements in *Xenopus* by Wnt/beta-catenin and Wnt/Ca2+ signaling. Mech Dev 2001, 106:61-76.
4. Gonzalez-Sancho J M, Brennan K R, Castelo-Soccio L A, Brown A M: Wnt Proteins Induce Dishevelled Phosphorylation via an LRP5/6-Independent Mechanism, Irrespective of Their Ability To Stabilize {beta}-Catenin. Mol Cell Biol 2004, 24:4757-4768.
5. Sheldahl L C, Slusarski D C, Pandur P, Miller J R, Kuhl M, Moon R T: Dishevelled activates Ca2+ flux, PKC, and CamKII in vertebrate embryos. J Cell Biol 2003, 161:769-777.
6. Clevers H: Wnt/beta-catenin signaling in development and disease. Cell 2006, 127:469-480.
7. Howe L R, Brown A M: Wnt signaling and breast cancer. Cancer Biol Ther 2004, 3:36-41.
8. van de Wetering M, Barker N, Harkes I C, van der Heyden M, Dijk N J, Hollestelle A, Klijn J G, Clevers H, Schutte M: Mutant E-cadherin breast cancer cells do not display constitutive Wnt signaling. Cancer Res 2001, 61:278-284.
9. Ugolini F, Adelaide J, Charafe-Jauffret E, Nguyen C, Jacquemier J, Jordan B, Birnbaum D, Pebusque M J: Differential expression assay of chromosome arm 8p genes identifies Frizzled-related (FRP1/FRZB) and Fibroblast Growth Factor Receptor 1 (FGFR1) as candidate breast cancer genes. Oncogene 1999, 18:1903-1910.
10. Veeck J, Niederacher D, An H, Klopocki E, Wiesmann F, Betz B, Galm O, Camara O, Durst M, Kristiansen G et al: Aberrant methylation of the Wnt antagonist SFRP1 in breast cancer is associated with unfavourable prognosis. Oncogene 2006, 25:3479-3488.
11. Klopocki E, Kristiansen G, Wild P J, Klaman I, Castanos-Velez E, Singer G, Stohr R, Simon R, Sauter G, Leibiger H et al: Loss of SFRP1 is associated with breast cancer progression and poor prognosis in early stage tumors. Int J Oncol 2004, 25:641-649.
12. Milovanovic T, Planutis K, Nguyen A, Marsh J L, Lin F, Hope C, Holcombe R F: Expression of Wnt genes and frizzled 1 and 2 receptors in normal breast epithelium and infiltrating breast carcinoma. Int J Oncol 2004, 25:1337-1342.
13. Ayyanan A, Civenni G, Ciarloni L, Morel C, Mueller N, Lefort K, Mandinova A, Raffoul W, Fiche M, Dotto G P et al: Increased Wnt signaling triggers oncogenic conversion of human breast epithelial cells by a Notch-dependent mechanism. Proc Natl Acad Sci USA 2006, 103:3799-3804.
14. Benhaj K, Akcali K C, Ozturk M: Redundant expression of canonical Wnt ligands in human breast cancer cell lines. Oncol Rep 2006, 15:701-707.
15. Lin S Y, Xia W, Wang J C, Kwong K Y, Spohn B, Wen Y, Pestell R G, Hung M C: Beta-catenin, a novel prognostic marker for breast cancer: its roles in cyclin D1 expression and cancer progression. Proc Natl Acad Sci USA 2000, 97:4262-4266.
16. Civenni G, Holbro T, Hynes N E: Wnt1 and Wnt5a induce cyclin D1 expression through ErbB1 transactivation in HC11 mammary epithelial cells. EMBO Rep 2003, 4:166-171.
17. Blobel C P: ADAMs: key components in EGFR signalling and development. Nat Rev Mol Cell Biol 2005, 6:32-43.
18. Prenzel N, Zwick E, Daub H, Leserer M, Abraham R, Wallasch C, Ullrich A: EGF receptor transactivation by G-protein-coupled receptors requires metalloproteinase cleavage of proHB-EGF. Nature 1999, 402:884-888.
19. Ohtsu H, Dempsey P J, Eguchi S: ADAMs as mediators of EGF receptor transactivation by G protein-coupled receptors. Am J Physiol Cell Physiol 2006, 291:01-010.
20. Roelle S, Grosse R, Aigner A, Krell H W, Czubayko F, Gudermann T: Matrix metalloproteinases 2 and 9 mediate epidermal growth factor receptor transactivation by gonadotropin-releasing hormone. J Biol Chem 2003, 278:47307-47318.
21. Bafico A, Liu G, Goldin L, Harris V, Aaronson S A: An autocrine mechanism for constitutive Wnt pathway activation in human cancer cells. Cancer Cell 2004, 6:497-506.
22. Hynes N E, Lane H A: ERBB receptors and cancer: the complexity of targeted inhibitors. Nat Rev Cancer 2005, 5:341-354.
23. Hart S, Fischer O M, Prenzel N, Zwick-Wallasch E, Schneider M, Hennighausen L, Ullrich A: GPCR-induced migration of breast carcinoma cells depends on both EGFR signal transactivation and EGFR-independent pathways. Biol Chem 2005, 386:845-855.
24. Motoyama A B, Hynes N E, Lane H A: The efficacy of ErbB receptor-targeted anticancer therapeutics is influenced by the availability of epidermal growth factor-related peptides. Cancer Res 2002, 62:3151-3158.

The invention claimed is:

1. A method of diagnosing cancer comprising the step of assessing the level of expression of teneurin-4 in a body fluid sample from a subject, wherein the level of teneurin-4 is determined using an antibody, and comparing said teneurin-4 expression level to a reference, wherein high levels of teneurin-4 constitute a diagnosis of cancer.

2. The method of claim 1 wherein the body fluid is blood, serum, plasma or cerebro-spinal fluid.

3. The method of claim 1 wherein the cancer is a cancer of the brain.

* * * * *

UNITED STATES PATENT AND TRADEMARK OFFICE
CERTIFICATE OF CORRECTION

PATENT NO.      : 8,642,280 B2                                            Page 1 of 1
APPLICATION NO. : 13/126802
DATED           : February 4, 2014
INVENTOR(S)     : Chiquet-Ehrismann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 216 days.

Signed and Sealed this

Twenty-ninth Day of September, 2015

Michelle K. Lee
*Director of the United States Patent and Trademark Office*